(12) United States Patent
Koepke

(10) Patent No.: US 9,204,872 B2
(45) Date of Patent: Dec. 8, 2015

(54) FULLY THREADED SUTURE ANCHOR WITH INTERNAL, RECESSED EYELETS

(75) Inventor: Ryan D. Koepke, Fort Wayne, IN (US)

(73) Assignee: Tornier, Inc., Bloomington, MN (US)

( * ) Notice: Subject to any disclaimer, the term of this patent is extended or adjusted under 35 U.S.C. 154(b) by 510 days.

(21) Appl. No.: 13/029,691

(22) Filed: Feb. 17, 2011

(65) Prior Publication Data

US 2012/0053626 A1     Mar. 1, 2012

Related U.S. Application Data

(60) Provisional application No. 61/305,464, filed on Feb. 17, 2010.

(30) Foreign Application Priority Data

Jun. 3, 2010  (FR) ...................... 10 54351

(51) Int. Cl.
*A61B 17/04*   (2006.01)
(52) U.S. Cl.
CPC ....... *A61B 17/0401* (2013.01); *A61B 2017/044* (2013.01); *A61B 2017/0414* (2013.01); *A61B 2017/0445* (2013.01); *A61B 2017/0459* (2013.01)
(58) Field of Classification Search
CPC ............... A61B 17/0401; A61B 2017/0414; A61B 2017/0448; A61B 2017/0446; A61B 2017/0445; A61B 2017/044; A61B 2017/0459
USPC ......................... 606/232, 300–321
See application file for complete search history.

(56) References Cited

U.S. PATENT DOCUMENTS

| | | | |
|---|---|---|---|
| 5,443,482 A | 8/1995 | Stone | |
| 5,464,427 A * | 11/1995 | Curtis et al. | ............. 606/232 |
| 6,045,573 A | 4/2000 | Wenstrom, Jr. et al. | |
| 6,149,653 A | 11/2000 | Deslauriers | |
| 6,610,080 B2 | 8/2003 | Morgan | |

(Continued)

FOREIGN PATENT DOCUMENTS

| | | |
|---|---|---|
| EP | 2036501 A2 | 3/2009 |
| JP | 2009-515653 | 4/2009 |

(Continued)

OTHER PUBLICATIONS

International Search Report issued in PCT/US06/44273 dated Aug. 3, 2007, 3 pages.

*Primary Examiner* — Christopher L Templeton
(74) *Attorney, Agent, or Firm* — Knobbe, Martens, Olson & Bear, LLP

(57) ABSTRACT

A suture anchor according to embodiments of the invention includes a body (102) having a proximal (121) and distal (125) ends and at least two suture paths open towards the proximal end and not open (e.g. looped around) towards the distal end and which are respectively capable of receiving a suture, and a proximal cavity (103) opening into a transverse cavity (104). The anchor may also include a transverse wall (105) arranged at least partially in the transverse cavity (104), and for each suture path, a distinct eyelet (112) for the passage of a suture through the transverse wall (105), so that a suture thread (162) in place in the anchor (100) forms a U with a first strand (162a) along the longitudinal axis (X-X), a second strand (162c) substantially parallel thereto, and an arc (162b) formed in the eyelet (112) and connecting the first and second strands.

29 Claims, 9 Drawing Sheets

(56) References Cited

U.S. PATENT DOCUMENTS

| | | | |
|---|---|---|---|
| 6,685,728 B2 | 2/2004 | Sinnott et al. | |
| 7,645,293 B2 * | 1/2010 | Martinek et al. | 606/232 |
| 7,713,285 B1 | 5/2010 | Stone et al. | |
| 7,976,565 B1 * | 7/2011 | Meridew | 606/232 |
| 8,029,536 B2 | 10/2011 | Sorensen et al. | |
| 8,083,769 B2 * | 12/2011 | Cauldwell et al. | 606/232 |
| 8,133,258 B2 * | 3/2012 | Foerster et al. | 606/232 |
| 2002/0120292 A1 | 8/2002 | Morgan | |
| 2003/0088250 A1 * | 5/2003 | Colleran et al. | 606/72 |
| 2004/0098053 A1 | 5/2004 | Tran | |
| 2005/0222619 A1 | 10/2005 | Dreyfuss et al. | |
| 2006/0122608 A1 | 6/2006 | Fallin et al. | |
| 2006/0235413 A1 * | 10/2006 | Denham et al. | 606/72 |
| 2007/0112352 A1 | 5/2007 | Sorensen et al. | |
| 2007/0135841 A1 * | 6/2007 | Dreyfuss | 606/232 |
| 2007/0225719 A1 * | 9/2007 | Stone et al. | 606/72 |
| 2009/0076545 A1 * | 3/2009 | DiMatteo et al. | 606/232 |
| 2010/0152773 A1 * | 6/2010 | Lunn et al. | 606/232 |
| 2011/0054526 A1 | 3/2011 | Stone et al. | |

FOREIGN PATENT DOCUMENTS

| | | |
|---|---|---|
| JP | 2009-101142 | 5/2009 |
| JP | 2009-531071 | 9/2009 |

* cited by examiner

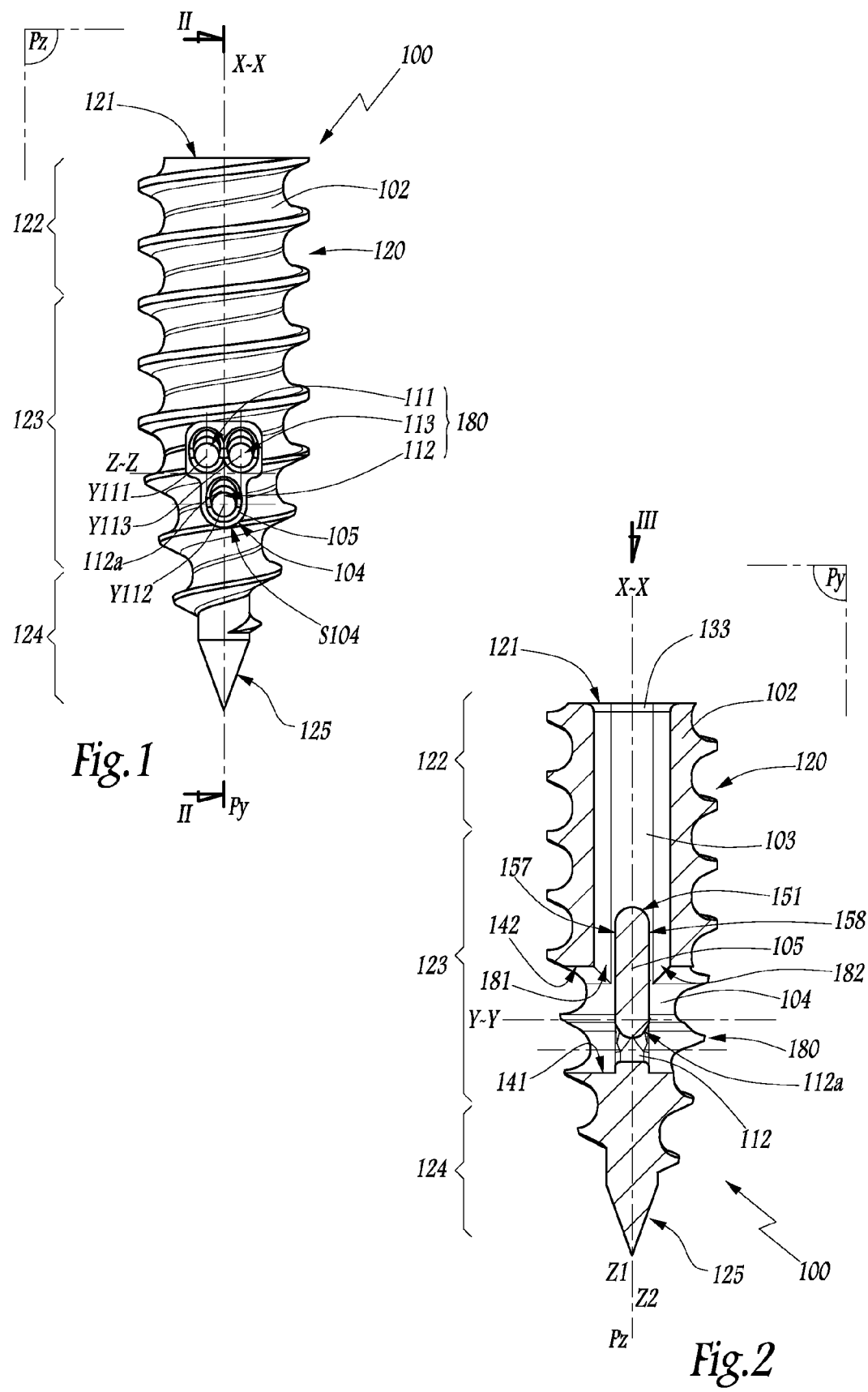

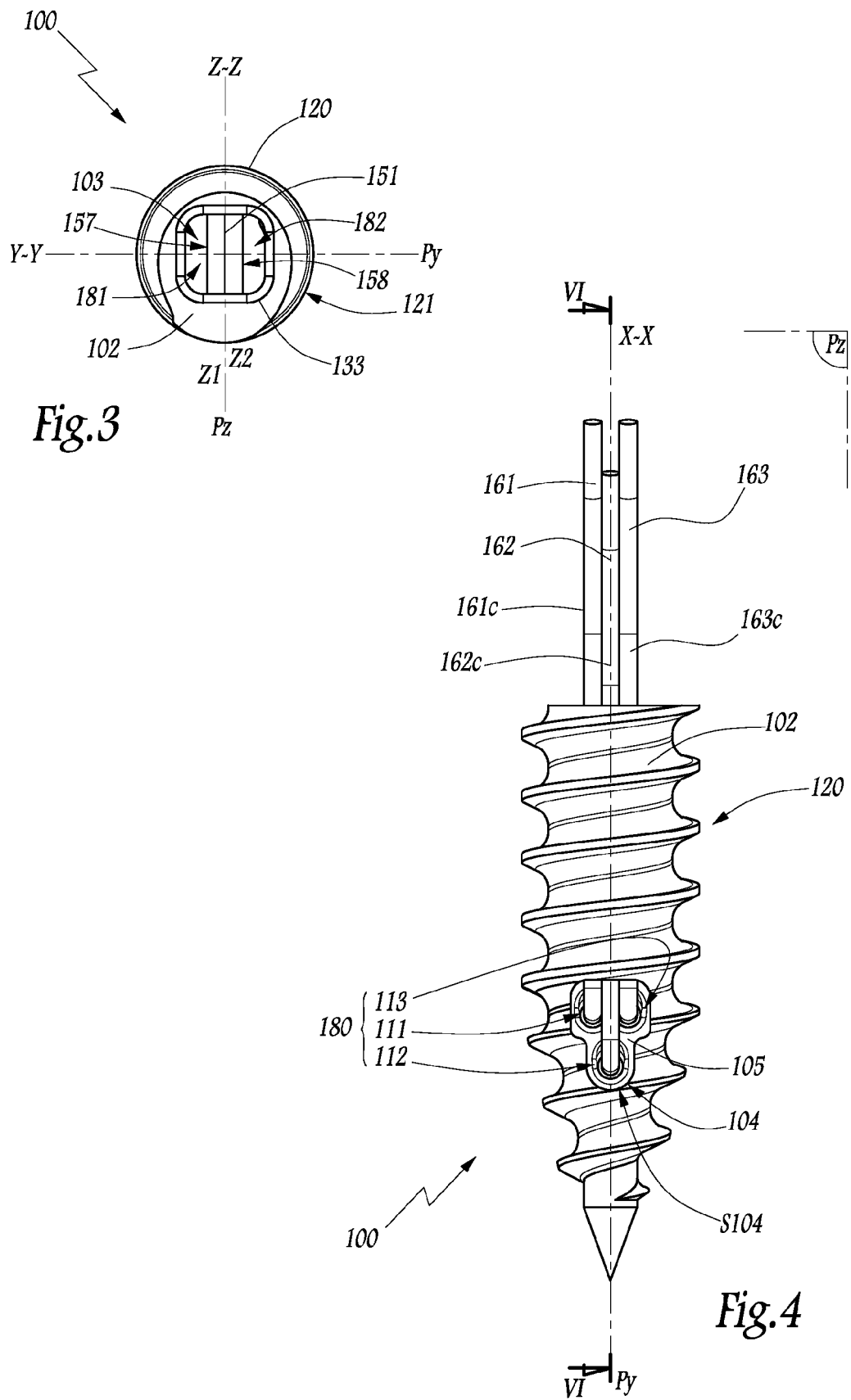

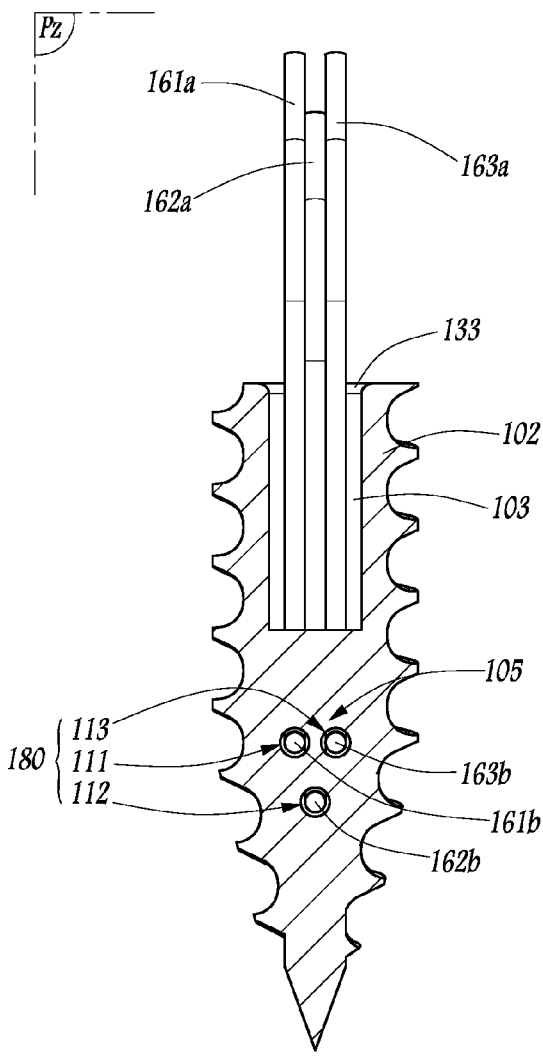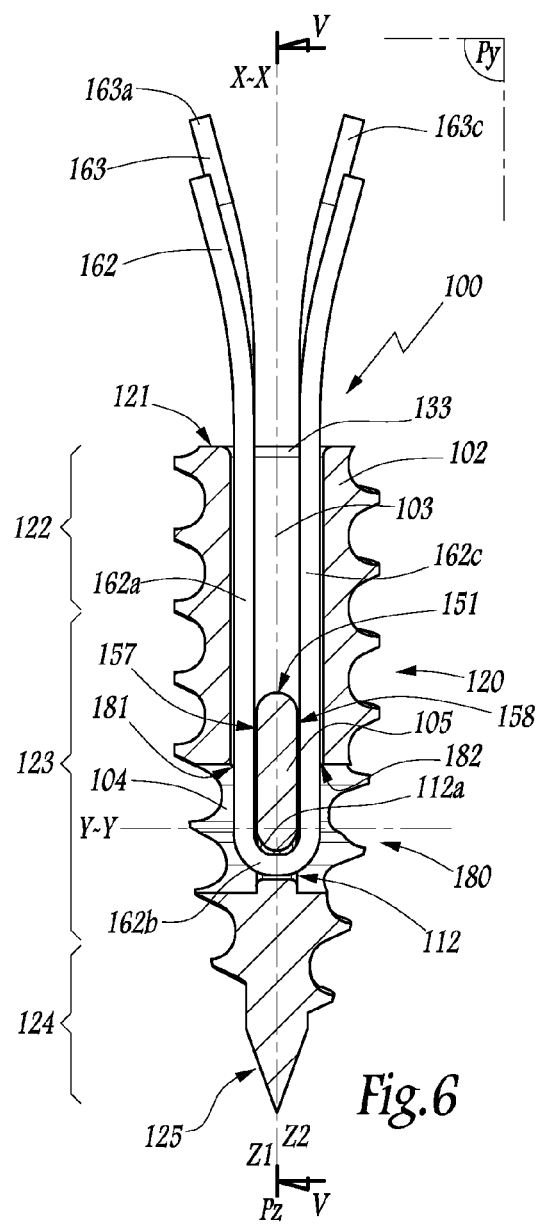
Fig.5
Fig.6

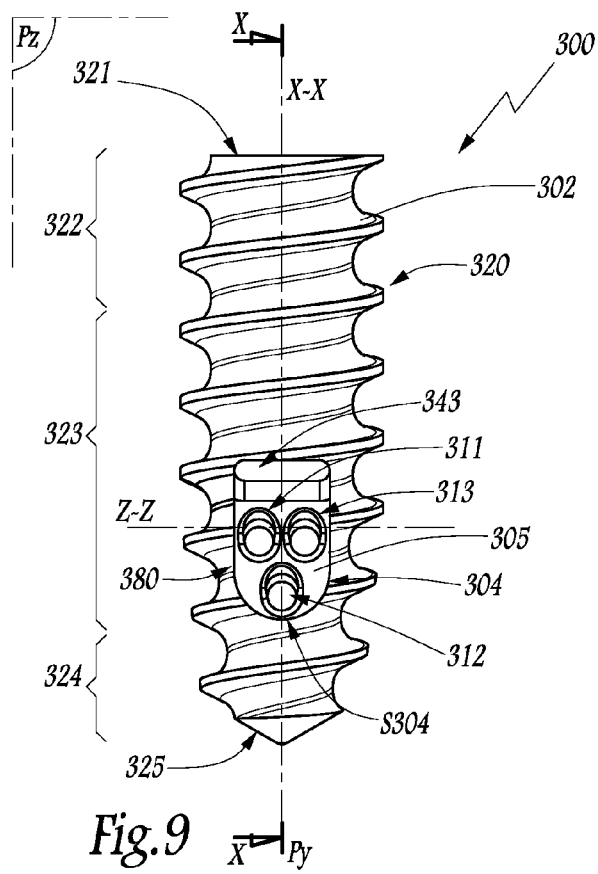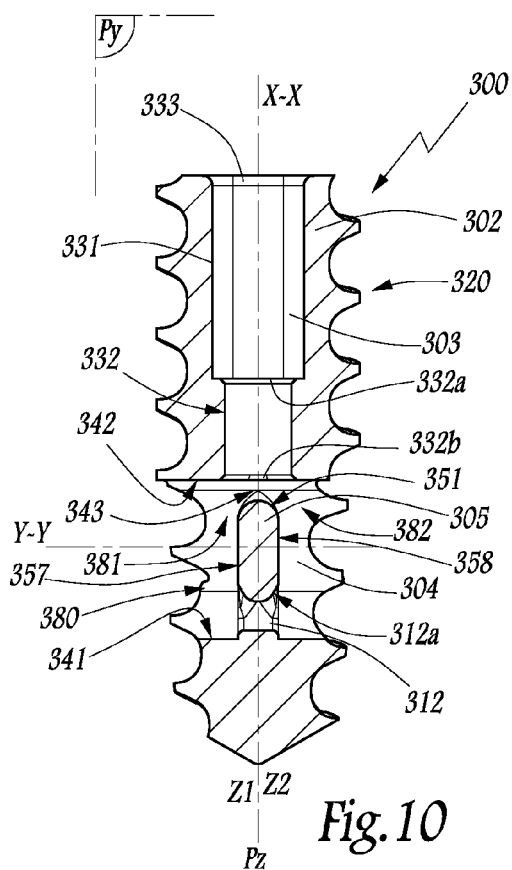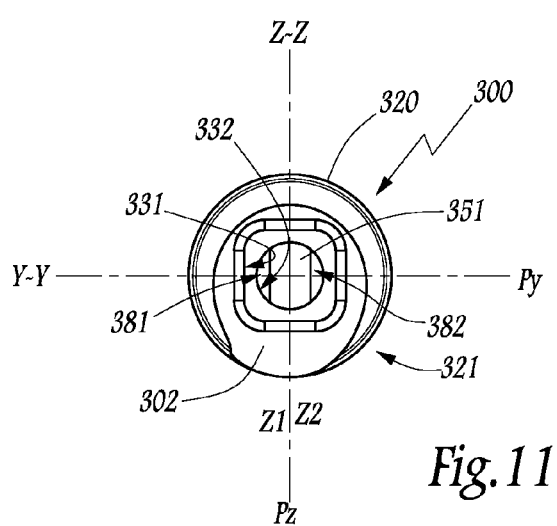

FULLY THREADED SUTURE ANCHOR WITH INTERNAL, RECESSED EYELETS

CROSS-REFERENCE TO RELATED APPLICATIONS

This application claims the benefit of U.S. Provisional Patent Application Ser. No. 61/305,464, filed Feb. 17, 2010, and claims foreign priority to French Patent Application Number 1054351, filed Jun. 3, 2010, both of which are incorporated by reference herein in their entireties for all purposes.

TECHNICAL FIELD

Embodiments of the present invention relate to suture anchors, and more particularly to suture anchors with internal recessed eyelets.

BACKGROUND

Suture anchors are often used for repairing a soft tissue, for example a muscle, a tendon or a ligament that has to be attached to a bone. When certain injuries take place, it is frequent that ligaments, tendons and other soft tissues are detached from the bones with which they are associated. Consequently, it becomes necessary to reattach the soft tissue to the bone in order to facilitate healing. The surgeon may have various devices for reattaching the soft tissue to the bone, such as screws, staples, pins, nails or even only a suture thread. A suture anchor can be anchored into the bone of the patient at the desired point of reattachment of the soft tissue, allowing a surgical suture thread to be attached. Such a suture anchor can be inserted into a bony cavity prepared for this purpose, or can be self-tapping.

After insertion into the bone, the anchor can be held in position by external elements, for example threading, ribs or excrescences of various types. These external elements provide a tension resistance so that the anchor is rigidly held in position during healing. Equally, such an anchor may comprise an eyelet, a bar, or another element for the attachment of the suture thread. Therefore, the free ends of the suture extend outside the bone, pass through or round the soft tissue and are used to attach the soft tissue to the bone.

However, certain known suture anchors, although effective in attaching a soft tissue to a bone, have a number of disadvantages. In practice, the anchor head may require sufficient dimensions to receive a driving tool, and to withstand the axial force and the torque generated by this driving tool when the anchor is inserted into the bone. Such an anchor has an increased length, and must be positioned in the bone at a sufficient depth to prevent the soft tissue from scraping against the exposed anchor head. However, once anchored, a tension applied to the anchor may cause it to migrate in the bone and cause the anchor head to come out of the bony cavity. This phenomenon of removal tension may cause a weakening of the attachment and a releasing of the soft tissues, and may even damage them. Moreover, the suture thread coming out of the anchor may rub against the edge of the bony cavity and be damaged.

SUMMARY

A threaded anchor provides an effective solution to the problem of removal tension. The body of such an anchor may comprise a loop or an internal bar for the attachment of the suture thread. As such, the suture thread is firmly attached and protected inside the body of the anchor, but it may not be able to slide independently and without jerkiness. Conversely, a sliding of the suture thread may affect the repair arrangement by changing the interface between the suture and the tissue, which may hamper healing. Moreover, when adjacent suture threads overlap and rub against one another, they can be damaged by friction and abrasion.

Some embodiments of the present invention solve one or more of the problems mentioned above: independent sliding and attachment of each suture thread, separation, and protection of the suture threads in the body of the anchor. Moreover, such an anchor may be compact, simple and cheap to manufacture.

Embodiments of the invention make it possible to obtain an improved suture anchor comprising suture paths protected in the body of the anchor, which allows easy handling and independent sliding of the suture threads. Friction and the risk of damage to the suture threads are reduced, while allowing the suture strands to be aligned in the same direction. Each eyelet corresponds to a single suture path, delimited in the body of the anchor and the transverse wall, according to embodiments of the present invention. Therefore, each suture thread can slide in the associated eyelet, while forming a 180° arc, without risk of overlap or friction between adjacent arcs and without risk of damage by the sharp ridges. Moreover, the arrangement of the eyelets and of the transverse wall makes it possible to produce an anchor that is compact and simple to manufacture.

A suture anchor according to some embodiments of the present invention includes an elongated body extending substantially along a longitudinal axis, and having a proximal end and a distal end; a proximal cavity formed in the body, the proximal cavity extending from the proximal end into the body; a transverse cavity formed in the body at least partially transversely to the longitudinal axis, between a first side of the body and a second side of the body opposite the first side, wherein the proximal cavity opens into the transverse cavity; a transverse wall at least partially spanning the transverse cavity, the transverse wall having a first face oriented toward the first side and a second face oriented toward the second side; a first eyelet extending through the transverse wall between the first face and the second face; and a second eyelet extending through the transverse wall between the first face and the second face, wherein the first and second eyelets are arranged such that a first suture may be inserted through the proximal cavity, over the first face, through the first eyelet, over the second face, and back through the proximal cavity, and a second suture may be inserted through the proximal cavity, over the first face, through the second eyelet, over the second face, and back through the proximal cavity. In some embodiments, the first and second eyelets both intersect the longitudinal axis and are substantially aligned longitudinally.

Suture anchor embodiments may further include a third eyelet extending through the transverse wall between the first face and the second face, wherein the first, second, and third eyelets are further arranged such that a third suture may be inserted through the proximal cavity, over the first face, through the third eyelet, over the second face, and back through the proximal cavity. According to such embodiments, the first and second eyelets may each extend through the transverse wall at a first position along the longitudinal axis, and the third eyelet may extend through the transverse wall at a second position along the longitudinal axis. In some cases, the first and second eyelets do not intersect the longitudinal axis, and the third eyelet intersects the longitudinal axis. The first and second eyelets may be located proximally with respect to the third eyelet. The first, second, and third eyelets may be independent of each other, such that a suture extending through one of the first, second, or third eyelets cannot pass into another of the first, second, or third eyelets without removal of the suture, according to some embodiments of the present invention.

An outer surface of the body may be threaded both proximally and distally of the transverse cavity. In some instances, the transverse wall extends into the proximal cavity, and in other instances, the transverse wall does not extend into the proximal cavity, thereby forming a transverse through-orifice between a proximal end of the transverse wall and a proximal face of the transverse cavity. According to some embodiments of the present invention, at least a portion of the proximal cavity is separated into two or more distinct cavity portions configured to receive separate sutures or separate strands of a same suture. For example, at least a portion of the proximal cavity may be separated into first, second, third, fourth, fifth, and sixth distinct cavity portions, such that the first cavity portion is configured to receive a first strand of the first suture, the second cavity portion is configured to receive a second strand of the first suture, the third cavity portion is configured to receive a first stand of the second suture, the fourth cavity portion is configured to receive a second strand of the second suture, the fifth cavity portion is configured to receive a first strand of the third suture, and the sixth cavity portion is configured to receive a second strand of the third suture. According to some embodiments of the present invention, the first and second eyelets are free of edges.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 is a view in elevation of a suture anchor according to an embodiment of the invention.

FIG. 2 is a section along the line II-II of FIG. 1, according to embodiments of the present invention.

FIG. 3 is a view in elevation in the direction of the arrow III of FIG. 2, according to embodiments of the present invention.

FIG. 4 is a view in elevation similar to FIG. 1 of the anchor furnished with the suture threads, according to embodiments of the present invention.

FIG. 5 is a longitudinal section of the anchor of FIGS. 1-4 in a plane parallel to the plane of FIG. 4, according to embodiments of the present invention.

FIG. 6 is a cross-sectional view taken along the line VI-VI of FIG. 4, and in which the section line V-V corresponding to FIG. 5 is indicated, according to embodiments of the present invention.

FIG. 9 is a view similar to FIG. 7 of a third embodiment of an anchor, according to embodiments of the present invention.

FIG. 10 is a section along the line X-X of FIG. 9, according to embodiments of the present invention.

FIG. 11 is a view in elevation in the direction of the arrow XI of FIG. 10, according to embodiments of the present invention.

Figure 7:
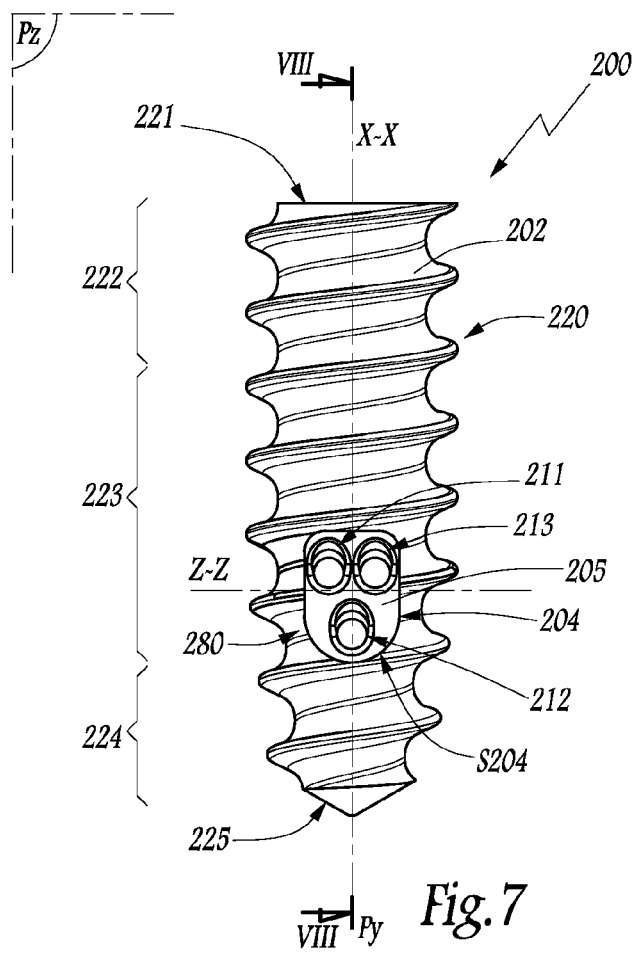
FIG. 7 is a view in elevation similar to FIG. 1 of another embodiment of a suture anchor.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Shown in FIGS. 1 to 6 is an embodiment of a suture anchor 100. The anchor 100 comprises a body 102 that is in one piece and elongated on a central longitudinal axis X-X. The body 102 comprises an outer surface 120 that is completely threaded, which has a constant maximum diameter from its proximal end 121, on its proximal portion 122 and its central span portion 123, and a progressively reduced diameter on its distal portion 124 in the direction of the distal end 125, which is in the form of a point. Included in the body 102 are a proximal cavity 103 and a transverse cavity 104.

In the direction of the length of the anchor 100, which is defined by the axis X-X, the central span portion 123 of the body 102 corresponds to the central region of the body 102, while the proximal portion 122 is close to the proximal end 121 and the distal portion 123 is close to the distal end 124. For example, as can be seen in FIGS. 1, 2 and 6, the proximal portion 122 represents the first quarter of the length, the central span portion 123 represents the central half of the length, and the distal portion 124 represents the last quarter of the length of the body 102. According to alternative embodiments not shown in FIGS. 1 to 6, the central span portion may extend for example over ⅔ or ⅗ of the length of the body.

The proximal cavity 103 extends parallel to the longitudinal axis X-X inside the body 102, from its central span portion 123 to its proximal end 121 at which the proximal cavity 103 opens to the outside. In FIGS. 1 to 6, the proximal cavity 103 has a cross section substantially in the shape of a square with rounded corners, and an axial symmetry relative to the longitudinal axis X-X. On the side of the proximal end 121, the border 133 of the proximal cavity 103 has a substantially rounded shape towards the outside and no sharp ridge.

According to other embodiments not shown in FIGS. 1 to 6, the cross section of the proximal cavity 103 is hexagonal. Specifically, the function of the cavity 103 may be to provide the interface between the anchor 100 and the point or operational end of a tool, and the latter can therefore have various cross-sectional shapes.

The transverse cavity 104 passes through the body 102 in its central span portion 123, while extending along a first transverse axis Y-Y which is substantially perpendicular to the longitudinal axis X-X. Its section S104 considered in the plane perpendicular to the axis Y-Y is substantially identical along the axis Y-Y, according to embodiments of the present invention. The proximal cavity 103 opens into the transverse cavity 104 at a proximal face 142 of the transverse cavity 104.

A transverse wall 105 is arranged in the transverse cavity 104 at the central span portion 123 of the body 102. The wall 105 extends in the direction of the proximal cavity 103 from a distal face 141 of the transverse cavity 104, and extends partially inside the proximal cavity 103 while terminating in an end 151 of rounded shape, which may also be referred to as the proximal end 151 of transverse wall 105. The wall 105 has a plane of symmetry Pz comprising the longitudinal axis X-X and a second transverse axis Z-Z which is perpendicular to the axes X-X and Y-Y. Therefore, the plane Pz delimits a first side Z1 and a second side Z2, as can be seen in FIGS. 2, 3 and 6. The wall 105 divides the transverse cavity 104 into two cavity portions situated on each side Z1 or Z2 of the plane Pz. The wall 105 extends essentially in the plane Pz and has two substantially flat faces 157 and 158, respectively on the side Z1 and on the side Z2. These faces 157 and 158 are parallel with one another and perpendicular to the first axis Y-Y. The dimensions of the wall 105 are smaller in the direction defined by this axis Y-Y than in the directions defined by the axes X-X and Z-Z. As an example shown in FIGS. 2 and 6, the length of the wall 105 along the axis X-X may be at least four times larger than the width of the wall 105 along the axis Y-Y. Therefore, the wall 105 can be qualified as a thin wall.

A plane Py is defined which comprises the longitudinal axis X-X and the first transverse axis Y-Y, and which is therefore perpendicular to the plane Pz. Therefore, by excluding the threaded outer surface 120, the planes Py and Pz are planes of symmetry of the anchor 100.

Arranged in the wall 105 are three through-eyelets 111, 112 and 113, which extend between the faces 157 and 158 substantially parallel to the axis Y-Y on respective axes Y111, Y112 and Y113, which are therefore perpendicular to the plane Pz. The axis Y112 of the eyelet 112 is secant with the axis X-X, while the axes Y111 and Y113 of the corresponding eyelets 111 and 113 are situated on either side of the axis X-X. As such, each eyelet 111, 112 and 113 passes through the plane Pz and connects the two sides Z1 and Z2. In other words, each eyelet 111, 112 and 113 passes through the wall 105 and opens on the faces 157 and 158.

As can be seen in FIGS. 4 to 6, several suture threads 161, 162, 163 can be arranged in the body 102 of the anchor 100, more precisely in respective suture paths. In the operational position, each thread 161, 162 or 163 comprises two strands that are substantially rectilinear and parallel, respectively a first strand 161a, 162a or 163a situated on the side Z1 and a second strand 161c, 162c or 163c situated on the side Z2, and an arc 161b, 162b or 163b formed in the corresponding eyelet 111, 112 or 113 and connecting the aforementioned two strands to one another.

When each suture thread 161, 162 or 163 is positioned in its specific suture path situated in the anchor 100, the first strand 161a, 162a or 163a enters the body 102 at the proximal end 121, and then passes through the proximal cavity 103 and the transverse cavity 104 while being substantially parallel to the longitudinal axis X-X. Then, in the central span portion 123 of the body 102, the thread 161, 162 or 163 passes through the wall 105 forming the arc 161b, 162b or 163b at 180° in the corresponding eyelet 111, 112 or 113, in which it can slide freely. Then the thread 161, 162 or 163 passes through the transverse cavity 104 and the proximal cavity 103 in the reverse direction in the form of the second strand 161c, 162c or 163c substantially parallel to the first strand 161a, 162a or 163a in order to exit the body 102 at the proximal end 121. In the connecting portion with the associated arc 161b, 162b or 163b, the rectilinear strand 161a, 162a or 163a runs along the face 157, while the rectilinear strand 161c, 162c or 163c runs along the face 158. Moreover, the first strand 161a, 162a or 163a passes through the proximal cavity 103 then the transverse cavity 104 by being positioned substantially on the side Z1, while the second strand 161c, 162c or 163c passes through the transverse cavity 104 then the proximal cavity 103 by being positioned substantially on the side Z2.

Thus, the anchor 100 comprises three suture paths which correspond respectively to the distinct eyelets 111, 112 and 113 and allow the threads 161, 162 and 163 to pass through. The suture paths are open towards the proximal end 121 and not open (e.g. loop around) towards the distal end 125. Each suture path has a portion 181 situated on the side Z1 for the passage of the first strand, a portion 182 situated on the side Z2 for the passage of the second strand, and a transverse space 180 which passes through the plane Pz and in which the arc of the suture thread is arranged. The proximal cavity 103, the transverse cavity 104 and the transverse wall 105 jointly delimit the suture paths, with the eyelets 111, 112 and 113. The transverse space 180 is capable of receiving at least one suture thread and is situated in the central span portion 123 of the body 102. In other words, in one embodiment, the eyelets 111, 112 and 113 delimit the transverse space 180 of the suture paths, while the lateral portions 181 and 182 of the suture paths extend from the eyelets on either side of the transverse wall 105, along the faces 157 and 158, in the direction of the proximal end 121. The wall 105 can therefore be referred to as a separating wall between the lateral portions 181 and 182 of the suture paths. At this wall 105, the rectilinear strands 161a, 162a, 163a, 161c, 162c and 163c extend along the respective faces 157 and 158 in the direction of the proximal wall 103 and of the proximal end 121.

The two eyelets 111 and 113 may be offset axially, that is to say in the direction defined by the longitudinal axis X-X, in the transverse wall 105 relative to the eyelet 112. Moreover, the two eyelets 111 and 113 are offset transversely from one another, in the direction defined by the axis Z-Z, in the transverse wall 105. In other words, the axes Y111, Y112 and Y113 of the three eyelets 111, 112 and 113 associated with the three suture paths define an isosceles triangle in the plane Pz, according to embodiments of the present invention. Thus, the eyelets 111, 112 and 113 are arranged in the wall 105 according to a compromise between the spacing of the suture paths and compactness of the anchor 100.

In practice, the transverse spacing of the eyelets 111, 112 and 113 makes it possible to prevent the suture strands 161a, 162a, 163a, 161c, 162c and 163c from crossing or overlapping, and thus rubbing against one another. As such, they are not worn under the effect of friction or abrasion, while being aligned substantially in the same direction. Since the arc 161b, 162b, 163b of each of the suture threads 161, 162, 163 is arranged inside the body 102 of the anchor 100, in its central span portion 123, it is better protected than if it were placed at one or other end 121 or 125 of the body 102 of the anchor 100.

As can be seen in FIGS. 2 and 6, the proximal face 112a of the eyelet 112, situated on the side of the proximal cavity 103, has a substantially parabolic convex shape. The same applies to the proximal faces of the eyelets 111 and 113, not shown. The borders of the eyelets have a substantially rounded shape and no sharp ridge. Thus, when the suture thread 161, 162 or 163 forms the arc 161b, 162b or 163b at 180° in the corresponding passageway eyelet 111, 112 or 113, it can rest on the proximal face of the eyelet in which it can slide without being damaged by sharp ridges.

The transverse cavity 104 extends on the side of the central span portion 123 which is closer to the distal portion 124 than to the proximal portion 122, emerging transversely on either side of the body 102. Because of this, the transverse cavity 104 and the wall 105, and therefore the transverse space 108 for passage of the threads 161, 162 and 163, are sufficiently distant from the distal end 125 to effectively protect the threads 161, 162 and 163. In addition, each thread 161, 162 or 163 is not held rigidly in position in the anchor 100. On the contrary, the sliding makes it easier for the surgeon to tie knots outside the anchor 100, according to some embodiments of the present invention.

In the embodiment illustrated in FIGS. 1 to 6, the profile of the section S104 of the transverse cavity 104, defined above, corresponds substantially to the arrangement of the three eyelets 111, 112 and 113, notably by following a curved profile, without sharp corners. The rounded shapes are easier to make in the body 102 of the anchor, for example by machining, notably piercing or milling, or by moulding. According to alternative embodiments of the present invention, not shown, the section S104 may be of a substantially rectangular, elliptical or triangular shape, notably with rounded corners.

The body 102 of the suture anchor 100 may be made of a metal, for example titanium. The titanium anchor 100 has considerable strength and biocompatibility properties, and is also furnished with a point which makes it easier to insert directly into the bone.

Figure 8:
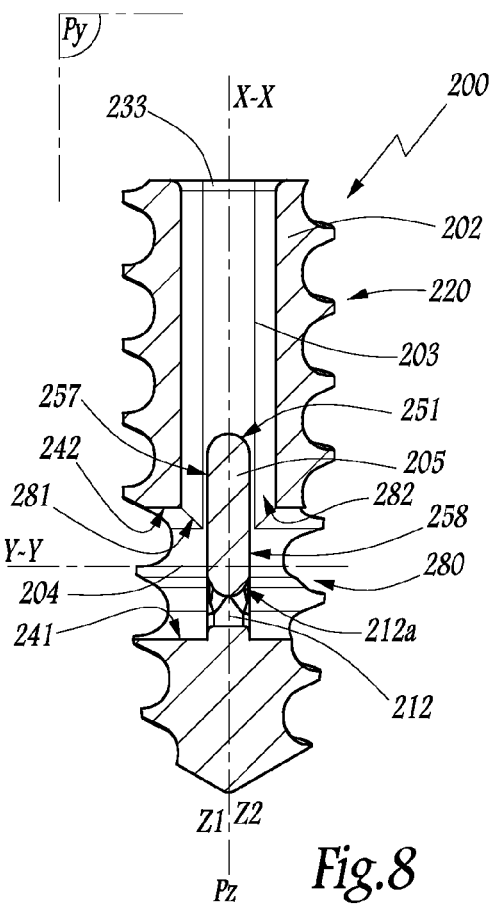
FIG. 8 is a section along the line VIII-VIII of FIG. 7, according to embodiments of the present invention.

FIGS. 7 and 8 show a suture anchor 200, according to embodiments of the present invention. Certain elements forming the anchor 200 are similar to the elements forming the anchor 100 of the embodiment, described above, and bear the same reference number increased by one hundred. These are the threaded outer surface 220 of the body 202, the proximal end 221, the proximal portion 222, the central span portion 223, the distal portion 224, the distal end 225, the proximal cavity 203, the distal face 241 and proximal face 242 of the transverse cavity 204, the rounded end 251 of the transverse wall 205, the faces 257 and 258, the eyelets 211, 212 and 213 and the parabolic proximal face 212a of the eyelet 212. The axes of the eyelets 211, 212 and 213 are not shown for the purpose of simplification.

In this embodiment, the anchor 200 comprises three suture paths which correspond respectively to the eyelets 211, 212 and 213. Each suture path is open towards the proximal end 221 and not open (e.g. loop around) towards the distal end 225. The eyelets 211, 212 and 213 delimit the transverse space 280 of the suture paths, while the lateral portions 281 and 282 of the suture paths extend from the eyelets on either side of the transverse wall 205, in the direction of the proximal end 221, respectively on the side Z1 and on the side Z2. The wall 205 extends essentially in the plane Pz, while the two faces 257 and 258 are substantially flat and perpendicular to the axis Y-Y. The axes of the three eyelets 211, 212 and 213 associated with the three suture paths define an isosceles triangle in the plane Pz.

The suture anchor 200 may be made of a polymer, for example polyether ether ketone (PEEK). A PEEK anchor 200 may have considerable properties of biocompatibility and of radio transparency and can be easily pierced during a revision, but its installation may require the prior formation of a bony cavity. Specifically, in comparison with the anchor 100, the reduction in diameter in the distal portion 224 is less pronounced, and the distal end 225 of the body 202 does not have a point distinct from the distal portion 204.

Moreover, as can be seen in FIG. 7, the section S204 of the transverse cavity 204 considered in a plane perpendicular to the transverse axis Y-Y is slightly different. The section S204 has a profile which corresponds substantially to the arrangement of the three eyelets 211, 212 and 213, with a portion of proximal profile of substantially rectangular shape with rounded corners, and a distal profile portion of rounded shape with no sharp corner. In practice, the profile of the section S204 is easier to make than the profile of the section S104 of the anchor 100, but one or other variant is suitable for a suture anchor according to embodiments of the invention.

FIGS. 9, 10 and 11 show a suture anchor 300. Certain elements forming the anchor 300 are similar to the elements forming the anchor 200 of the embodiment, described above, and bear the same reference numbers increased by one hundred. They are the threaded outer surface 320 of the body 302, the proximal end 321, the proximal portion 322, the central span portion 323, the distal portion 324, the distal end 325, the distal face 341 and proximal face 342 of the transverse cavity 304, the rounded end 351 of the transverse wall 305, the faces 357 and 358, the eyelets 311, 312 and 313 and the parabolic proximal face 312a of the eyelet 312.

In this embodiment, the anchor 300 comprises three suture paths which correspond respectively to the eyelets 311, 312 and 313. Each suture path is open towards the proximal end 321 and not open (e.g. loop around) towards the distal end 325. The eyelets 311, 312 and 313 delimit the transverse space 380 of the suture paths, while the lateral portions 381 and 382 of the suture paths extend from the eyelets on either side of the transverse wall 305 in the direction of the proximal end 321, respectively on the side Z1 and on the side Z2. The wall 305 extends essentially in the plane Pz, while the two faces 357 and 358 are substantially flat and perpendicular to the axis Y-Y. As an example shown in FIG. 10, the length of the wall 305 along the axis X-X is nearly three times larger than the width of the wall 305 along the axis Y-Y. The axes of the three eyelets 311, 312 and 313 associated with the three suture paths define an isosceles triangle in the plane Pz.

As can be seen in FIG. 10, the proximal cavity 303 comprises two distinct portions 331 and 332 extending along the longitudinal axis X-X of the body 302 of the anchor 300. The first cavity portion 331 is arranged on the side of the proximal end 321, and has a transverse section of substantially square shape with rounded corners. The second cavity portion 332 is arranged between this first cavity portion 331 and the transverse cavity 304, and has a transverse section of substantially circular shape. Each of the longitudinal ends 332a and 332b of the second cavity portion 332 has a chamfered border, in particular of substantially rounded shape and with no sharp ridge, so as not to damage the suture threads 361, 362 and 363 when they pass through.

The section S304 of the transverse cavity 304 is larger than the section S204 of the anchor 200. Unlike the anchors 100 and 200, the body 302 comprises in its central span portion 323 a transverse through-orifice 343 other than the eyelets 311, 312 and 313 passing through the transverse wall 305. This orifice 343 makes the anchor 300 easier to manufacture, for example by making it possible to use a bit with larger dimensions in order to produce a cannulation in the body 302.

The transverse wall 305 is arranged inside the transverse cavity 304 and does not extend, even partially, into the proximal cavity 303, according to embodiments of the present invention. On the side oriented towards the proximal end 321, the end 351 of the transverse wall 305 is rounded in a convex manner in the plane Py, and in a concave manner in the plane Pz, so as to have no sharp ridge capable of damaging the suture threads, according to embodiments of the present invention.

When the suture threads are positioned in the anchor 300, like the threads 161, 162 and 163 mentioned above in relation to the anchor 100, a first strand of each thread enters the body 302 at the proximal end 321, then passes through the first portion 331 and the second portion 332 of the proximal cavity 303 and the transverse cavity 304 while being substantially parallel to the longitudinal axis X-X. Then, in the central span portion 323 of the body 302, each thread passes through the wall 305 forming a 180° arc in the corresponding eyelet 311, 312 or 313 in which it can slide freely. Then each thread passes through the transverse cavity 304 and the first portion 331 and the second portion 332 of the proximal cavity 303 in the reverse direction, in the form of a second strand substantially parallel to the aforementioned first strand, in order to exit from the body 302 at the proximal end 321. Thus, these suture threads are combined in the second portion 332 of the proximal cavity 303, but without overlapping and rubbing excessively against one another.

Figure 12:
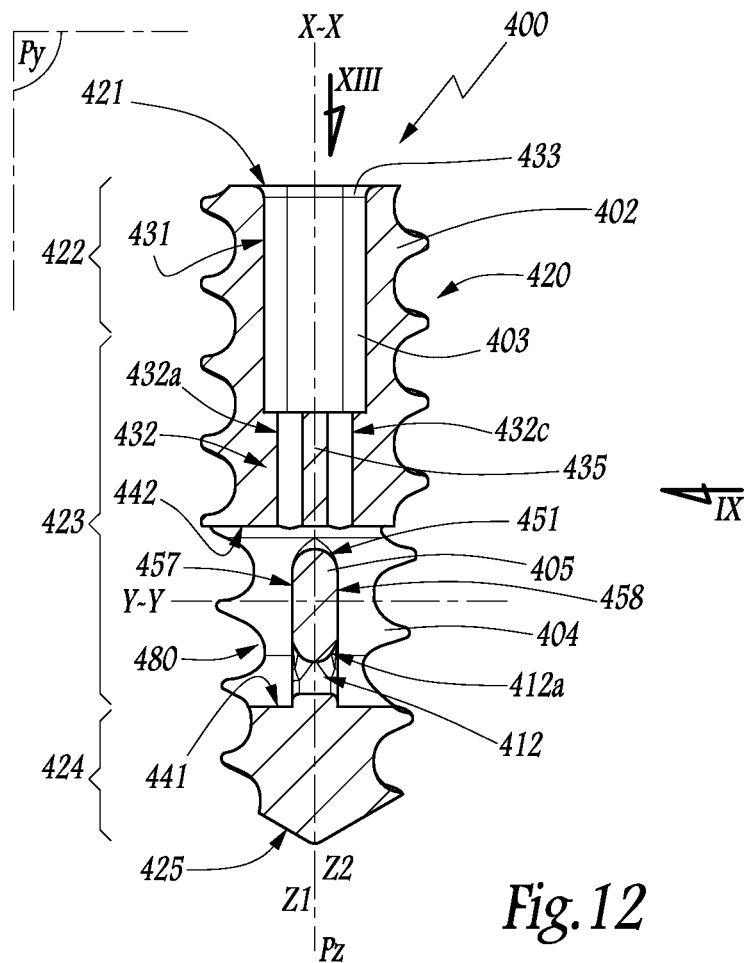
FIG. 12 is a section similar to FIG. 10 of another embodiment of a suture anchor.
Figure 13:
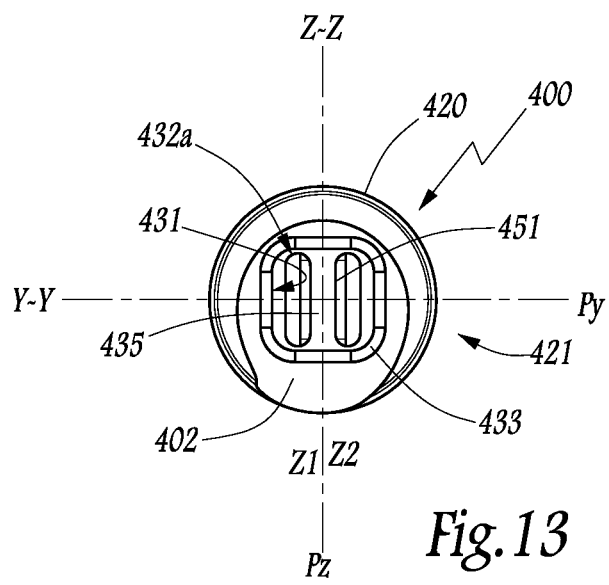
FIG. 13 is a view in elevation in the direction of the arrow XIII of FIG. 12, according to embodiments of the present invention.

FIGS. 12 and 13 show a suture anchor 400 according to embodiments of the present invention. Certain elements forming the anchor 400 are similar to the elements forming the anchor 300 of the embodiment, described above, and bear the same reference numbers increased by one hundred. These are the threaded outer surface 420 of the body 402, the proximal end 421, the proximal portion 422, the central span portion 423, the distal portion 424, the distal end 425, the distal face 441 and proximal face 442 of the transverse cavity 404, the section S404, the rounded end 451 of the transverse wall 405, the faces 457 and 458, the eyelets 411, 412 and 413 and the parabolic proximal face 412a of the eyelet 412.

If the anchor 400 is observed in the direction of the arrow IX of FIG. 12, it reveals a view in elevation similar to FIG. 9. In comparison with the anchor 300, the proximal cavity 403 of the anchor 400 also comprises two distinct cavity portions 431 and 432, but the second cavity portion 432 comprises two orifices 432a and 432c separated by a wall 435. Each of the orifices 432a and 432c has a cross section of substantially rectangular shape, of which the wide ends parallel to the axis Z-Z are linear, and of which the narrow ends are rounded. The longitudinal walls of larger dimensions of the orifices 432a and 432c are parallel to the plane Pz, and hence parallel to the longitudinal faces of the transverse wall 405 which are parallel to the plane Pz. In other words, the separating wall 435 extends parallel to the plane Pz. The first orifice 432a is adapted to receive on the side Z1 the first strand of each of the suture threads, while the second orifice 432c is adapted to receive on the side Z2 the second strand of each of the suture threads, not shown.

In practice, the first strands are grouped together and the second strands are grouped together, but the first are separated from the second in their respective orifice 432a or 432c, situated on either side of the wall 435. Therefore, the risk of overlap or of friction, and therefore of damaging the suture threads, is more limited. As such, the anchor 400 comprises three suture paths which correspond respectively to the eyelets 411, 412 and 413. Each suture path is open towards the proximal end 421 and not open (e.g. loop around) towards the distal end 425. In this embodiment, the eyelets 411, 412 and 413 delimit the transverse space 480, while the orifices 432a and 432c form the lateral portions of the suture paths, open towards the proximal end 421 and not open (e.g. loop around) towards the distal end 425. The wall 405 extends essentially in the plane Pz, while the two faces 457 and 458 are substantially flat and perpendicular to the axis Y-Y. The axes of the three eyelets 411, 412 and 413 associated with the three suture paths define an isosceles triangle in the plane Pz, according to embodiments of the present invention.

Figure 14:
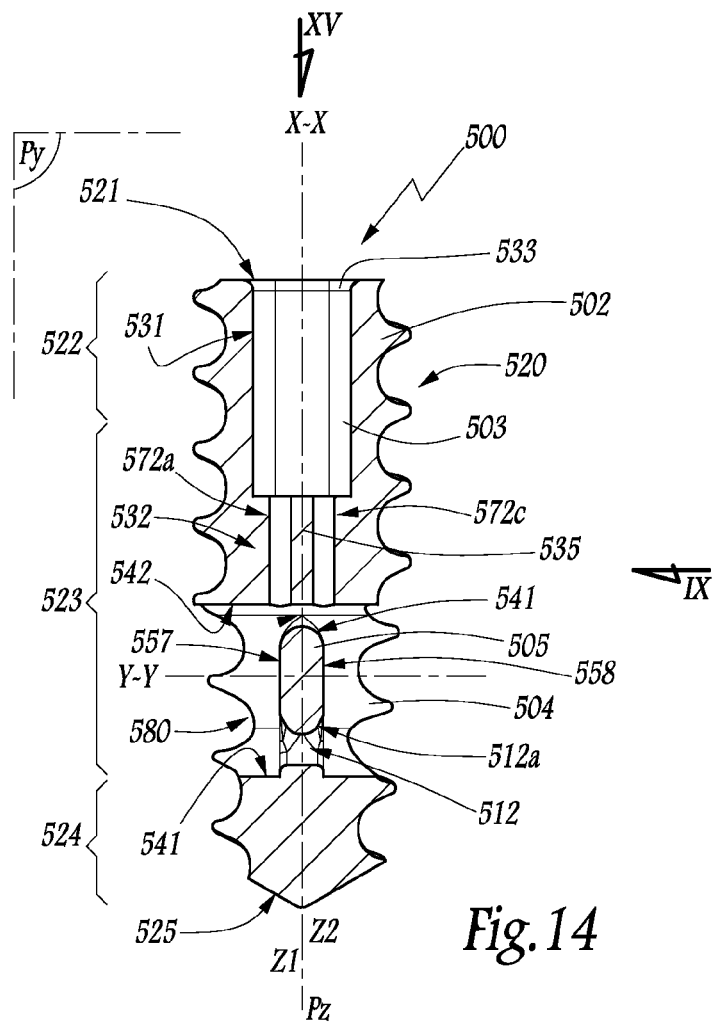
FIG. 14 is a section similar to FIG. 10 of another embodiment of a suture anchor.
Figure 15:
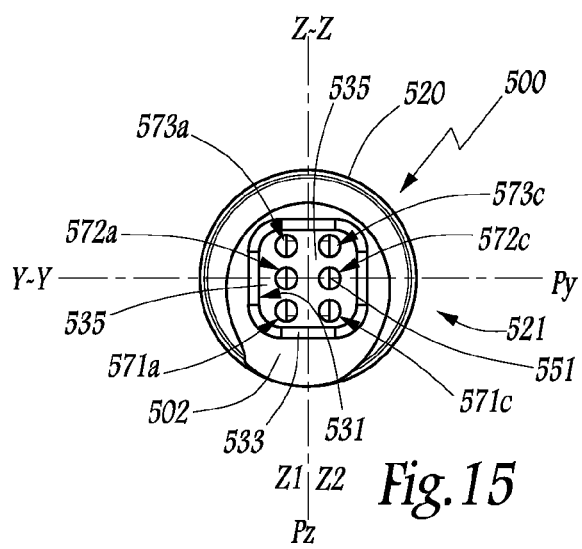
FIG. 15 is a view in elevation in the direction of the arrow XV of FIG. 14, according to embodiments of the present invention.

FIGS. 14 and 15 show a suture anchor 500, according to embodiments of the present invention. Certain elements forming the anchor 500 are similar to the elements forming the anchor 400 of the embodiment, described above, and bear the same reference numbers increased by one hundred. These are the threaded outer surface 520 of the body 502, the proximal end 521, the proximal portion 522, the central span portion 523, the distal portion 524, the distal end 525, the distal face 541 and proximal face 542 of the transverse cavity 504, the section S504, the rounded end 551 of the transverse wall 505, the faces 557 and 558, the eyelets 511, 512 and 513, and the parabolic proximal face 512a of the eyelet 512.

If the anchor 500 is observed along the arrow IX of FIG. 14, it shows a view in elevation similar to FIG. 9. In comparison with the anchors 300 and 400, the proximal cavity 503 of the anchor 500 also comprises two distinct cavity portions 531 and 532, but the second cavity portion 532 comprises six longitudinal orifices 571a, 572a, 573a, 571c, 572c and 573c, which extend parallel to the longitudinal axis X-X. Each of the orifices has a cross section of circular shape, with a diameter slightly greater than the diameter of the suture threads (not shown). Each eyelet corresponds to two orifices, which are arranged in the second portion 532 of the proximal cavity 503 in symmetry with the plane Pz, and of which the respective axes are secant with the axis of the corresponding eyelet. The first orifice is adapted to receive the first strand of the corresponding suture thread, while the second orifice is adapted to receive the second strand of the corresponding suture thread (not shown).

In practice, the anchor 500 comprises three suture paths which correspond respectively to the eyelets 511, 512 and 513. Each suture path is open towards the proximal end 521 and not open (e.g. loop around) towards the distal end 525. Each strand of each suture thread has its own through-orifice 571a, 572a, 573a, 571c, 572c or 573c in the proximal cavity 503, and can follow its own suture path without contact with the other threads in the cavity portion 532. Thus, the risk of overlap and of friction, and hence of damaging the suture threads, is even more limited than for the anchors 300 and 400.

The wall 505 extends essentially in the plane Pz, while the two faces 557 and 558 are substantially flat and perpendicular to the axis Y-Y. The axes of the three eyelets 511, 512 and 513 associated with the three suture paths define an isosceles triangle in the plane Pz. In addition, a separating wall 535 that can be seen in FIGS. 14 and 15 is defined that is situated in the cavity portion 532, which extends parallel to the plane Pz and which separates the three orifices 571a, 572a and 573a situated on the side Z1 of the three orifices 571c, 572c and 573c which are situated on the side Z2. In this embodiment, the eyelets 511, 512 and 513 delimit the transverse space 580, while the orifices 571a, 572a, 573a, 571c, 572c and 573c form the lateral portions of the suture paths, open towards the proximal end 521 and not open (e.g. loop around) towards the distal end 525.

Figure 16:
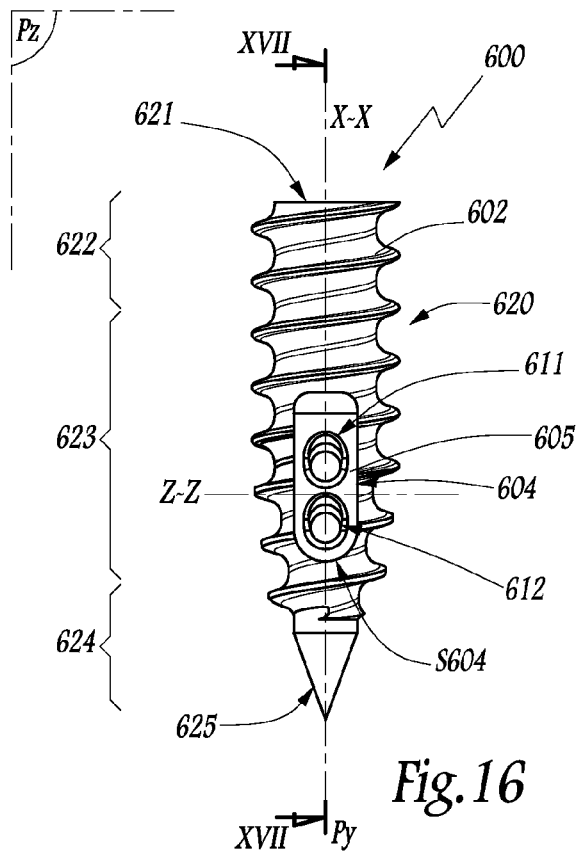
FIG. 16 is a view similar to FIG. 1 of another embodiment of the invention.
Figure 17:
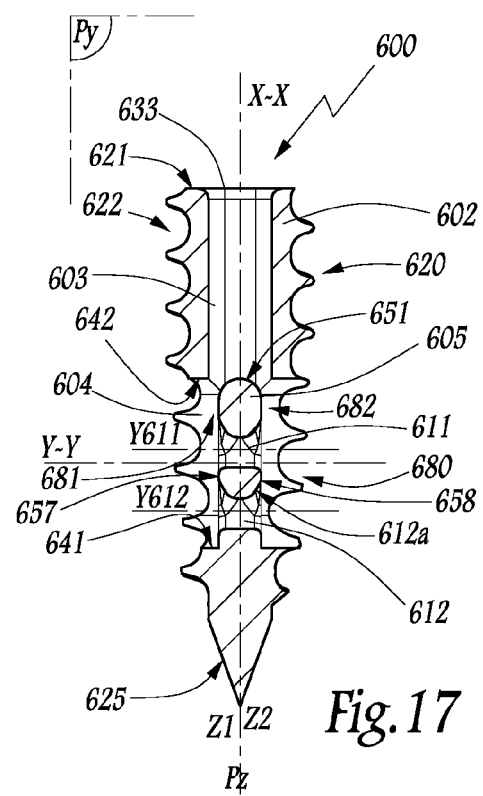
FIG. 17 is a view in section in the direction of the arrow XVII of FIG. 16, according to embodiments of the present invention.

FIGS. 16 and 17 show a suture anchor 600 according to embodiments of the present invention. Certain elements forming the anchor 600 are similar to the elements forming the anchor 100 of the embodiments, described above, and bear the same reference numbers increased by one hundred. These are the threaded outer surface 620 of the body 602, the proximal end 621, the proximal portion 622, the central span portion 623, the distal portion 624, the distal end 625, the proximal cavity 603, the distal face 641 and proximal face 642 of the transverse cavity 604, the section S604, the rounded end 651 of the transverse wall 605, the faces 657 and 658 and the parabolic proximal face 612a of the eyelet 612.

The body 602 of the anchor 600 has a smaller diameter than body 102, for example. Thus, in the present case, only two eyelets 611 and 612 are arranged in the transverse wall 605, and as a result the anchor 600 comprises only two suture paths, according to some embodiments of the present invention. The two eyelets 611 and 613 are offset axially in the transverse wall 605. Each suture path is open towards the proximal end 621 and not open (e.g. loop around) towards the distal end 625. Two suture threads, not shown, can then each form an arc in the respective eyelet 611 or 612 and can extend to the outside of the body 602 passing through the transverse cavity 604 and the proximal cavity 603. The axes Y611 and Y612 of the two eyelets 611 and 612 are substantially parallel with one another and perpendicular and secant with the longitudinal axis X-X.

In this embodiment, the eyelets 611 and 612 delimit the transverse space 680, while the lateral portions 681 and 682 of the suture paths are situated respectively on the side Z1 and on the side Z2, open towards the proximal end 621 and not open (e.g. loop around) towards the distal end 625. According to alternative embodiments, not shown, the reduction in diameter in the distal portion 624 is less pronounced, and the distal end 625 of the body 602 does not have a point distinct from the distal portion 604. According to yet other embodiments, not shown, the proximal cavity 603 may comprise two distinct portions arranged in a manner similar to one of the anchors 300, 400 and 500 and suitable for the arrangement in the anchor 600 of only two eyelets 611 and 612 and two suture threads.

Figure 18:
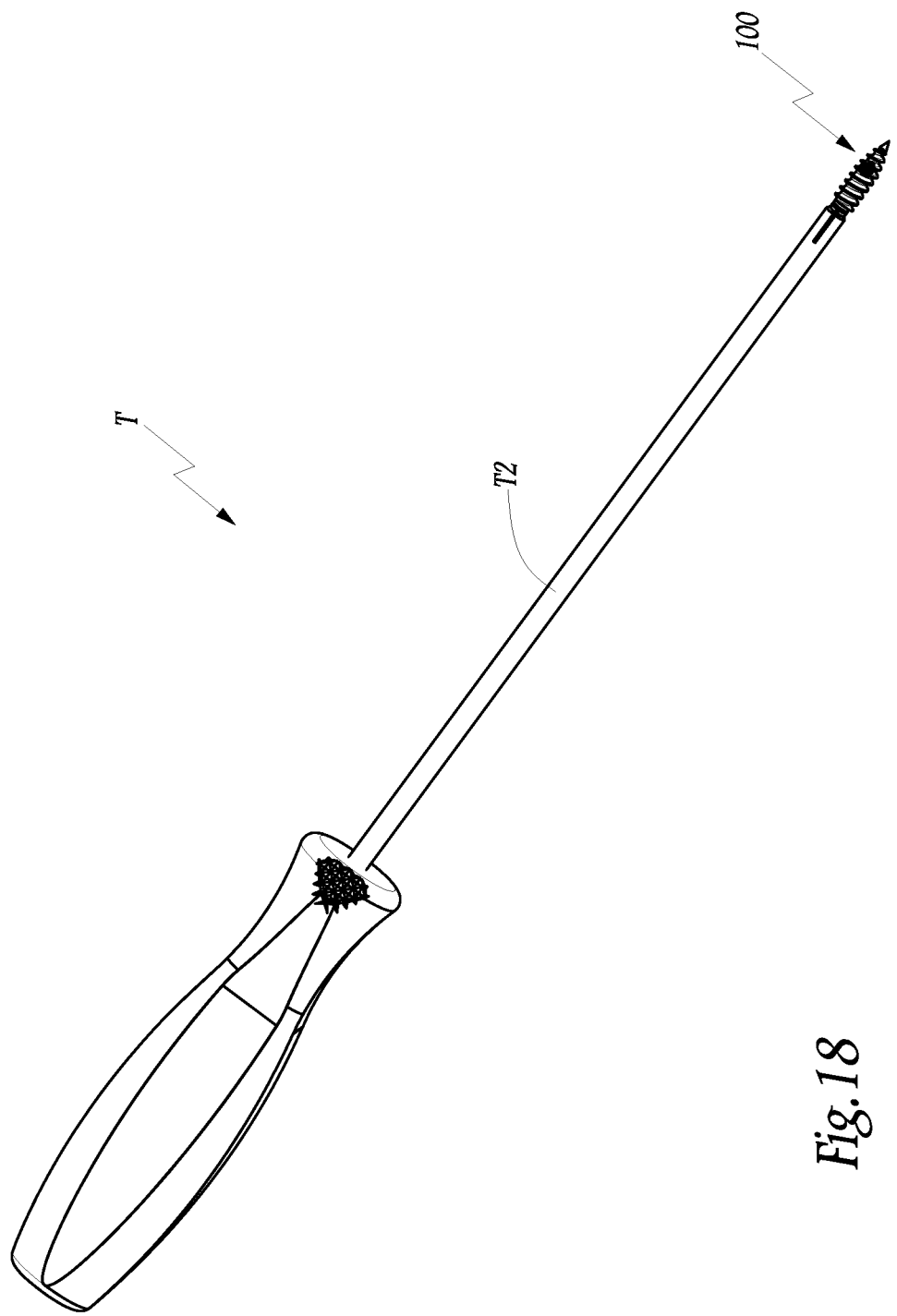
FIG. 18 is a view in perspective of the suture anchor of FIGS. 1 to 6 coupled with a driving tool, according to embodiments of the present invention.

FIG. 18 shows the suture anchor 100 and a tool T used for installing the suture anchor 100 in the bone of the patient (not shown). In practice, a longitudinal stem T2 of the tool T is housed in the proximal cavity 103 of the body 102 of the anchor 100, in order to be able to transmit thereto a rotary movement and a torque. In particular, the point of the stem T2 is suitable for being inserted into a cavity 103 having a hexagonal and/or square section, according to some embodiments of the present invention. The suture threads 161, 162 and 163 are positioned in the anchor 100 before the latter is placed at the end of the stem T2 of the tool T. Since the outer surface 120 of the body 102 of the anchor 100 is threaded, the tool T may be a screwdriver.

According to an alternative embodiment, not shown, the tool may be of any type suitable for installing the suture anchor into the bone of the patient, by imparting a rotary movement thereto. Such a tool is generally suitable for a single diameter of anchor, but it may be suited to any type of anchor, of variable diameter.

The anchors 100, 200, 300, 400, 500 and 600 may be made of polymer, for example polyether ether ketone (PEEK), or of metal, for example titanium. Depending on the strength of the material and the configuration with or without point, the anchor may be placed in a bony cavity prepared before its insertion, or may otherwise be self-tapping. According to some embodiments of the present invention, the body of the anchors (including the transverse wall) is in one single unitary piece, which makes them easier to manufacture. According to an alternative embodiment, certain elements are fitted or overmoulded into the anchor body. In this case, the anchor may be formed without any sharp ridge capable of damaging the suture threads.

According to another embodiment, the anchor is only partially threaded. In some instances, the anchor may comprise more than three eyelets for threading as many suture threads, arranged in different manners in the body of the anchor, in the transverse wall. The configuration according to one or more embodiments can be adapted to the number of eyelets and to their arrangement. Each suture thread has its own suture path, according to some embodiments of the present invention.

According to one alternative embodiment of the anchor 400, the walls 405 and 435 may be indistinguishable, and comprise eyelets 411, 412 and/or 413. Similarly for the anchor 500, the walls 505 and 535 may be formed in a single piece and may have a configuration similar to the aforementioned variant of the anchor 400.

In general, embodiments of the present invention may include suture paths that are delimited, on the one hand, by the transverse wall or walls and the eyelets and, on the other hand, by the transverse cavity and the proximal cavity. No existing suture anchor protects the suture threads with comparable effectiveness, while providing for easy handling and independent sliding of these threads.

According to some embodiments of the invention, the suture paths extend on either side of the transverse wall, and are open towards the proximal end and not open (e.g. loop around) towards the distal end. The transverse space is capable of receiving at least one suture thread, is situated in the central span portion of the body, and passes through the reference plane Pz. Specifically, each anchor according to embodiments of the present invention comprises at least one transverse wall which extends substantially in the plane Pz and which is arranged at least partially in the transverse cavity and/or the proximal cavity. This transverse wall may be the wall 105, 205, 305, 405, 505 or 605 defined above, comprising eyelets. Various configurations of the suture anchor, notably of the transverse wall or walls and of the transverse space, can be employed without departing from the context of the invention.

Therefore, the suture paths have a geometry and are positioned in the body of the anchor so that a suture thread in place in the anchor forms a U with a first rectilinear strand which is engaged both in the proximal cavity and in the transverse cavity, on a first side Z1 of the reference plane Pz, a second rectilinear strand which is engaged both in the proximal cavity and in the transverse cavity, on a second side Z2 of the reference plane Pz, while being substantially parallel to the first strand, and an arc which is engaged in the transverse space and which connects the first strand and the second strand, from the first side Z1 to the second side Z2 of the reference plane Pz.

Some or all of the technical features of the various embodiments may be combined together. Therefore, the anchor can be adapted to a particular application, notably in terms of cost, of simplicity of use and of performance.

During the repair of a soft tissue, the risk of damage to the suture threads or a sharp or pointed portion of the anchor is greatly reduced in embodiments of the present invention. The anchor is simple and cheap to manufacture and is of reduced size. Moreover, the threading provides good resistance to the tension of withdrawal. Therefore, the suture anchor according to some embodiments of the invention can be anchored firmly in the bony mass of the patient, which promotes healing and provides the surgeon with additional assurance.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A suture anchor comprising:
a body, wherein the body is elongated, extends along a longitudinal axis, and comprises a proximal end and a distal end;
a proximal cavity formed in the body, the proximal cavity extending from the proximal end into the body;
a transverse cavity formed in the body at least partially transversely to the longitudinal axis, between a first side of the body and a second side of the body opposite the first side, wherein the proximal cavity opens into the transverse cavity;
a transverse wall at least partially spanning the transverse cavity, the transverse wall having a first face oriented toward the first side and a second face oriented toward the second side;
a first eyelet extending through the transverse wall between the first face and the second face; and
a second eyelet extending through the transverse wall between the first face and the second face, wherein the first and second eyelets are arranged such that a first suture may be inserted through the proximal cavity, over the first face, through the first eyelet, over the second face, and back through the proximal cavity, and a second suture may be inserted through the proximal cavity, over the first face, through the second eyelet, over the second face, and back through the proximal cavity;
wherein the first and second eyelets are intersected by an axis that is perpendicular to the longitudinal axis of the body;
a third eyelet extending through the transverse wall between the first face and the second face, wherein the first, second, and third eyelets are further arranged such that a third suture may be inserted through the proximal cavity, over the first face, through the third eyelet, over the second face, and back through the proximal cavity
wherein the first and second eyelets each extend through the transverse wall at a first position along the longitudinal axis, and wherein the third eyelet extends through the transverse wall at a second position along the longitudinal axis;
wherein the first and second eyelets are located between the proximal end and the third eyelet.

2. The suture anchor of claim 1, wherein the first, second, and third eyelets are independent of each other, such that a suture extending through one of the first, second, or third eyelets cannot pass into another of the first, second, or third eyelets without removal of the suture.

3. The suture anchor of claim 1, wherein an outer surface of the body is threaded both proximally and distally of the transverse cavity.

4. The suture anchor of claim 1, wherein the transverse wall extends into the proximal cavity.

5. The suture anchor of claim 1, wherein the transverse wall does not extend into the proximal cavity, thereby forming a transverse through-orifice between a proximal end of the transverse wall and a proximal face of the transverse cavity.

6. The suture anchor of claim 1, wherein at least a portion of the proximal cavity is separated into two or more distinct cavity portions configured to receive separate sutures or separate strands of a same suture.

7. The suture anchor of claim 1, wherein at least a portion of the proximal cavity is separated into a first, second, third, fourth, fifth, and sixth distinct cavity portion, wherein the first distinct cavity portion is configured to receive a first strand of the first suture, the second distinct cavity portion is configured to receive a second strand of the first suture, the third distinct cavity portion is configured to receive a first stand of the second suture, the fourth distinct cavity portion is configured to receive a second strand of the second suture, the fifth distinct cavity portion is configured to receive a first strand of the third suture, and the sixth distinct cavity portion is configured to receive a second strand of the third suture.

8. The suture anchor of claim 1, wherein the first and second eyelets are free of edges.

9. The suture anchor of claim 1, wherein the transverse wall has a longitudinal dimension from a distal end of the transverse wall to a proximal end of the transverse wall, the proximal end of the transverse wall being at the transverse cavity, the transverse wall having a thickness extending between the first and second faces, the longitudinal dimension being at least about four times greater than the thickness.

10. The suture anchor of claim 1, wherein the first eyelet, the second eyelet, and the third eyelet define a triangle.

11. The suture anchor of claim 1, further comprising distinct, enclosed orifices disposed between the proximal end and the transverse cavity, each orifice extending parallel to the longitudinal axis of the body, wherein the first suture may be inserted through a first enclosed orifice of the distinct enclosed orifices, over the first face, through the first eyelet, over the second face, and through a second enclosed orifice of the distinct enclosed orifices, and the second suture may be inserted through a third enclosed orifice of the distinct enclosed orifices, over the first face, through the second eyelet, over the second face, and through a fourth enclosed orifice of the distinct enclosed orifices.

12. The suture anchor of claim 1, wherein the proximal cavity has a first enclosed orifice having a first cross-sectional shape and a second enclosed orifice having a second cross-sectional shape, different than the first cross-sectional shape.

13. A suture anchor system, comprising:
a suture thread; and
an elongated body having a proximal end and a distal end, the body including at least three suture paths which are open towards the proximal end and not open towards the distal end and which are respectively capable of receiving the suture thread,
a proximal cavity which is included in the body and which extends on a longitudinal axis of the body, and
a transverse cavity which extends on a first axis that is transverse to the longitudinal axis and wherein the proximal cavity opens into the transverse cavity,
a transverse wall which is arranged at least partially in the transverse cavity and which extends along the longitudinal axis and on a second axis that is transverse to the longitudinal axis and the first axis, and
a first, second and third eyelet for the passage of the suture thread, wherein each eyelet passes through the transverse wall while extending along an axis parallel to the first axis, wherein when the suture thread is in place in the anchor, the suture thread forms a U-shape and is comprised of:
a first rectilinear strand extending parallel to the longitudinal axis,
a second rectilinear strand opposite to the first strand, and
an arc formed in one of the eyelets and connecting the first rectilinear strand and the second rectilinear strand,
wherein the axes of the first, second and third eyelets define an isosceles triangle in a plane comprising the longitudinal axis and the second axis.

14. The suture anchor system according to claim 13, wherein the transverse wall extends in a plane comprising the longitudinal axis and the second axis, and has two faces parallel with one another and perpendicular to the first axis, the rectilinear strands extending partly along these two faces.

15. The suture anchor system according to claim 13, wherein the transverse wall extends in the direction of the proximal cavity from a distal face of the transverse cavity.

16. The suture anchor system according to claim 13, wherein the transverse wall extends partially inside the proximal cavity.

17. The suture anchor system according to claim 13, wherein at least two of the eyelets are offset in the transverse wall in a direction of the second axis.

18. The suture anchor system according to claim 13, wherein the body includes three suture paths which are open towards the proximal end and not open towards the distal end.

19. The suture anchor system according to claim 13, wherein the proximal cavity comprises a first cavity portion which has a hexagonal-shaped cross section.

20. The suture anchor system according to claim 19, wherein the proximal cavity also comprises a second cavity portion with two orifices.

21. The suture anchor system according to claim 19, wherein the proximal cavity also comprises a second cavity portion, wherein at least two orifices are arranged symmetrically relative to the plane comprising the longitudinal axis and the second axis.

22. The suture anchor system according to claim 13, wherein each eyelet has an arcuate-shaped wall in a plane comprising the longitudinal axis and the first axis.

23. The suture anchor system according to claim 13, wherein the body is in one piece.

24. The suture anchor system according to claim 13, wherein the body is made of a polymer.

25. The suture anchor system according to claim 24, wherein the polymer is polyether ether ketone (PEEK).

26. The suture anchor system according to claim 13, wherein the body is made of metal.

27. The suture anchor system according to claim 26, wherein the metal is titanium.

28. The suture anchor system of claim 13, wherein the proximal cavity comprises distinct, enclosed orifices that extend parallel to the longitudinal axis of the body.

29. The suture anchor system of claim 13, wherein the proximal cavity has a first enclosed orifice having a first cross-sectional shape and a second enclosed orifice having a second cross-sectional shape, different than the first cross-sectional shape.

* * * * *